US00PP10275P

United States Patent [19]

Nevo

[11] Patent Number: Plant 10,275

[45] Date of Patent: Mar. 10, 1998

[54] 'SHUFRA' PISTACHIO TREE

[76] Inventor: Amram Nevo, Post Office Box 500, Omer, 84965, Israel

[21] Appl. No.: 739,494

[22] Filed: Oct. 28, 1996

[51] Int. Cl.[6] ..... A01H 5/00

[52] U.S. Cl. ..... Plt./30.1

[58] Field of Search ..... Plt./30.1

[56] References Cited

U.S. PATENT DOCUMENTS

P.P. 4,953 11/1982 Anderson et al. ..... Plt./30.1
P.P. 4,994 3/1983 Anderson et al. ..... Plt./30.1
P.P. 5,837 12/1986 Anderson et al. ..... Plt./30.1

OTHER PUBLICATIONS

UPOVROM Disk 1997/03 UPOVROM Citation for 'Shufra' IL PBR 01653, accepted Jan. 13, 1991, 1997.

*Primary Examiner*—James R. Feyrer
*Assistant Examiner*—Kent L. Bell
*Attorney, Agent, or Firm*—Worrel & Worrel

[57] ABSTRACT

A new and distinct variety of pistachio tree which is somewhat remotely similar to the 'Kerman' pistachio tree, but from which it is distinguished in a number of respects including by producing its crop with many fewer hours of winter chilling, by having more compact configurations permitting the trees of the new variety to be planted in patterns of greater density, by producing a crop which is mature for harvesting and shipment in Omer, Israel approximately eight days prior to the crop of the 'Kerman' pistachio tree, and by producing a crop which equals or exceeds the quality of that of the 'Kerman' pistachio tree in nearly all respects.

2 Drawing Sheets

BACKGROUND OF THE NEW VARIETY

The present invention relates to a new and distinct variety of pistachio tree, *Pistacia vera* which will hereinafter be denominated varietally as the 'Shufra' pistachio tree, and, more particularly, to a pistachio tree which produces a crop of exceptional quality, which is mature for commercial harvesting and shipment approximately August 16 to September 14 in Omer, Israel.

The discovery and development of new commercial varieties of pistachio trees presents particular difficulties. Frequently such varieties are discovered in countries of the Middle East which may make their introduction into the Unites States difficult. More significantly, many varieties of pistachio trees, grown principally for their commercial crop, do not produce such crops in sufficient volume, quality, or regularity of bearing to be commercially viable. Many such varieties produce nuts in which the shell does not split, or does not split sufficiently, in a high enough percentage of cases to have commercial appeal. Other chronic deficiencies include too high a percentage of nuts in which there is no kernel within the shell or where the nuts are otherwise defective. Finally, in many varieties of pistachio trees the flavor of the kernels is bland or otherwise lacks appeal and is therefore unacceptable for most usages.

The pistachio tree of the instant variety, by contrast, appears to excel in many of the attributes in which other known varieties are lacking.

ORIGIN AND ASEXUAL REPRODUCTION OF THE NEW VARIETY

The present variety of pistachio tree hereof was discovered by the inventor in 1982 as a newly found seedling in his orchard which was a designed plot of pistachio seedlings located in Omer, Israel. The parentage of the newly found seedling was an undefined, open pollinated female tree. The new variety was first asexually reproduced by the inventor in the orchard of origin in Omer, Israel in 1984. Such asexual reproduction was achieved by budding on young rootstocks of the *Pistachia atlantica* variety and by top working some mature trees. The inventor has continuously observed the asexually reproduced trees and confirmed that they are in all respects identical to the parent tree.

SUMMARY OF THE NEW VARIETY

The 'Shufra' pistachio tree is characterized by producing an excellent quality nut with an orange hull coloration, a vivid dark red pellicle and a deep green kernel and which is ripe for commercial harvesting and shipment approximately August 16 to September 14 in Omer, Israel. The new variety is somewhat remotely similar to the 'Kerman' pistachio tree, but is distinguishable therefrom in numerous respects including by the aforementioned ripening date which is about eight days earlier than the 'Kerman' pistachio tree in Israel.

BRIEF DESCRIPTION OF THE DRAWING

The drawing consists of three photographs of the new variety of the present invention including a first photograph, designated "FIG. 1," showing mature fruit of the new variety growing on a branch thereof in a typical pattern; a second photograph, designated "FIG. 2," showing foliage of the subject variety growing in a manner representative thereof; and a third photograph, designated "FIG. 3," showing mature fruit of the new variety including a first in its natural outer hull, a second with the outer hull removed with the kernel left in place in the shell, a third wherein the kernel is whole and fully exposed having had the hull, shell and pellicle removed, a fourth in which the fully exposed kernel has been separated along the suture thereof and laid open to expose the interior thereof, and a fifth in which the kernel with its pellicle in place has been sectioned along a plane substantially right-angularly related to the suture plane thereof.

DETAILED DESCRIPTION

Figure 2:
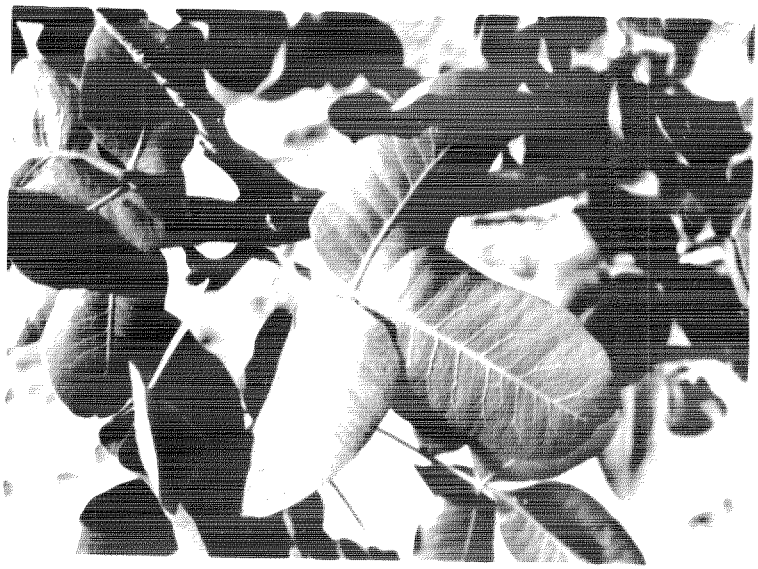
Figure 1:
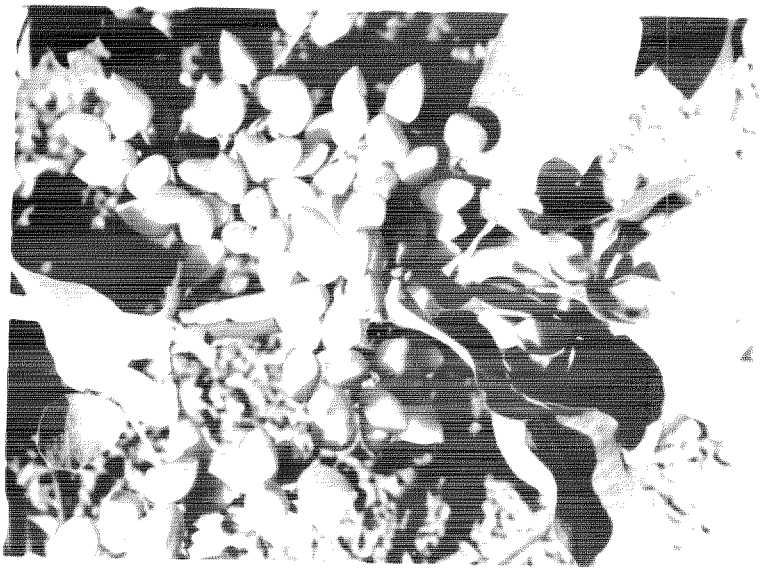
Figure 3:
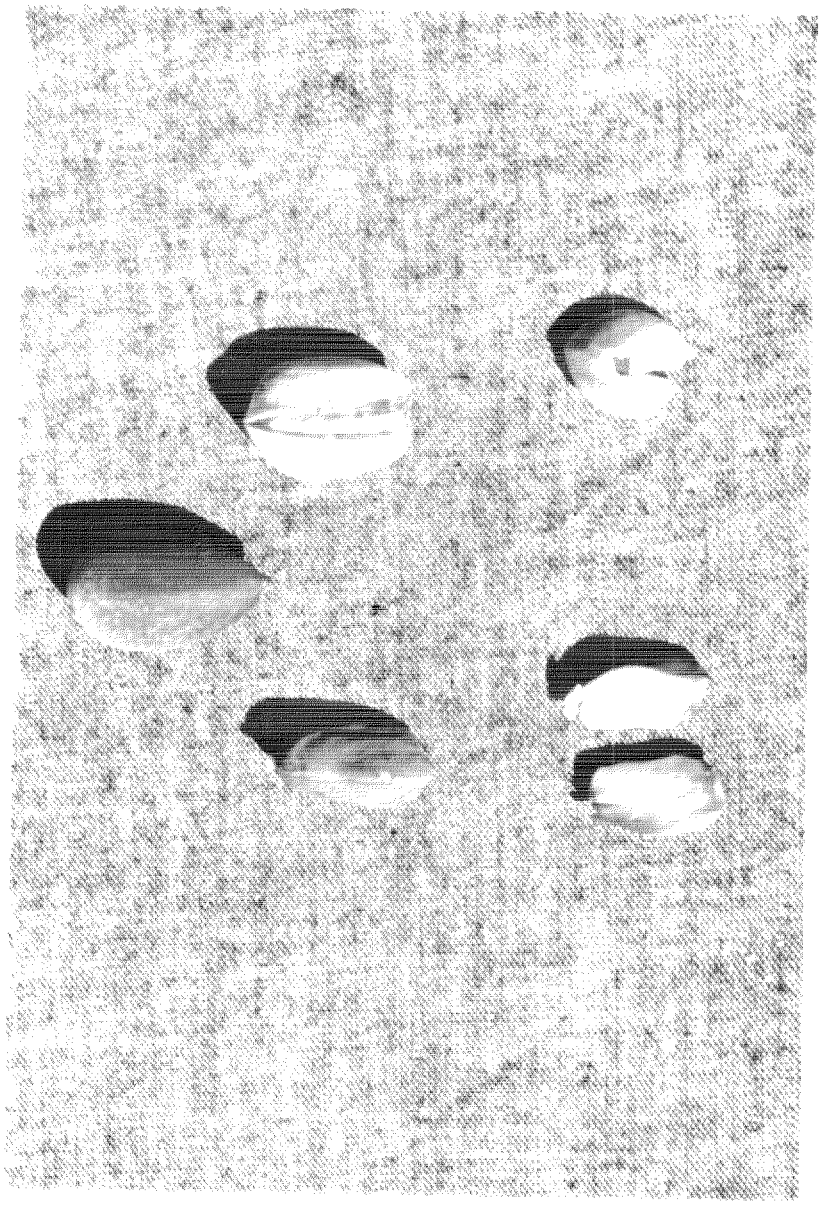

Referring more specifically to the botanical details of this new and distinct variety of pistachio tree, the following has been observed under the ecological conditions prevailing at the orchid of origin which is located in Omer, Israel. All major color code designations are by reference to the *Nickerson Color Fan* produced by the Munsell Color Company Incorporated. Common color names are also occasionally employed.

TREE

Generally:

The tree as described herein is twelve (12) years of age. It is budded on *Pistachia atlantica* rootstock.

*Size—height.*—2.75 m (9.1 feet). The tree is compact permitting planting of an increased number of trees per unit of land. As compared with the 'Kerman' pistachio tree, ten percent (10%) to twenty percent (20%) more trees can be grown per unit of land. Thus, there is a comparative increase in crop yield per unit of land.

*Size—diameter.*—2.5 m (8.3 feet).

*Vigor.*—High.

*Chilling requirements.*—The new variety produces top quality nuts under climatic conditions in which other known varieties of pistachio trees of the same category cannot produce such a crop. For example, the 'Kerman' pistachio tree requires at least 800 hours of winter chilling (up to 7° C.). Preferably, the 'Kerman' variety has 1000 to 1200 hours of winter chilling in a season. The instant variety, by contrast, produces well at 500 hours of winter chilling. If a dormancy breaking treatment is applied, the instant variety can produce well under conditions as low as 440 hours of winter chilling. As a consequence, extensive new geographical areas will be available for pistachio nut production. Similarly, the production of this variety in geographical areas with over 500 hours of chilling will be substantially enhanced.

*Figure.*—The trees were trained and shaped for harvesting by hand; that is, on a low trunk of about 40 cm (1.3 ft.) high.

*Productivity.*—The parent tree, in twelve (12) consecutive years from the age of six (6) years until the age of seventeen (17), has yielded a total of 67.0 kilograms of dry in shell nuts. In the sixth year, the yield was 0.4 kilogram. In the seventeenth year, the yield was 9.7 kilograms. There is a clear pattern for alternate bearing. Some of the asexually reproduced trees of the new variety were grafted on *Pistachia atlantica* rootstock and some on *Pistachia vera* rootstock. As the trees have developed, there is no difference in shape or yield between the two. However, those grafted on *Pistachia atlantica* rootstock are slightly larger.

*Density.*—Good.

*Regularity of bearing.*—Alternate.

Trunk:

*Size.*—Height—40 cm (1.6 feet).

*Characteristics.*—At 30 cm (1 foot) above ground.

*Diameter.*—11.5 cm (4.6 inches).

*Surface texture.*—Rather rough.

*Color.*—5 YR (6/1).

*Lenticels—number.*—Numerous.

*Lenticels—size.*—1.8 mm (0.072 inches).

Branches:

*Size.*—Main Scaffold—26 mm (1.06 inches) to 40 mm (1.6 inches).

*Surface texture—mature.*—Rough.

*Color—one year or older wood.*—5 YR (7/2).

*Surface texture—immature growth.*—Smooth.

*Color—Immature branches.*—10 YR (4/4).

*Lenticels—numbers.*—Quite few.

*Lenticels—size.*—0.8 mm (0.032 inches) to 1.8 mm (0.072 inches).

LEAVES

Size:

*Generally.*—Compound. Mostly trifoliate, but there are also leaves of 1, 2 and 4 leaflets.

*Foliage.*—Abound.

*Leaflets.*—Average length—Of the central leaflet—8 cm (3.2 inches) to 13 cm (5.2 inches). Of the side leaflets—5 cm (2 inches) to 8 cm (3.2 inches). Average Width—Of the central leaflet—4 cm (1.6 inches) to 8 cm (3.2 inches). Of the side leaflets—2.5 cm (1 inch) to 5.5 cm (2.2 inches).

Shape: Elliptic. Rather flat. Minutely cuspidate.

Thickness: 0.2 mm (0.008 inches) to 0.4 mm (0.016 inches).

Color:

*Upwardly disposed surface.*—2.5 GY (5/5).

*Downwardly disposed surface.*—2.5 GY (4/3).

Marginal Form:

*Generally.*—Entire.

Leaf vein—thickness: Midrib, 1.8 mm (0.072 inches) to 0.2 mm (0.008 inches). Laterals, 0.4 mm (0.016 inches) to 0.1 mm (0.004 inches).

Color—leaf vein: 2.5 GY (9/8).

Leaf glands: Practically none.

Petiole:

*Length.*—3 cm (1.2 inches) to 5.5 cm (2.2 inches).

*Thickness.*—1.5 mm (0.06 inches) to 3 mm (0.12 inches).

*Color.*—2.5 GY (8/9).

Petiolar sinus: 120° to 140°.

Stipules: None.

FLOWERS

Date of bloom: First receptive stigmas the first week of April. More and more are coming on for ten to twelve days.

Bloom amount: In accordance with alternate bearing, abundant on "on" years and less on "off" years.

Size:

*Flowers—generally.—Each single flower* 2 mm (0.08 inches) to 3 mm (0.12 inches) in diameter.

*Blossom.*—Medium producing 30 to 60 nuts per cluster. The actual total number of flowers in each blossom is much higher, but a large portion thereof never set fruit.

Petals:

*Color.*—Whole blossom green.

*Stigmas.*—Cream.

FRUIT

Maturity when described: Selective hand harvesting August 16 to September 14. Mechanical harvesting about September 5 in Omer, Israel. The optimal set day for mechanical harvesting appears to be eight (8) days earlier than the 'Kerman' pistachio tree.

Productivity: Very good. The new trees of the instant variety start beating a crop one year earlier than the new trees of the 'Kerman' pistachio variety.

Distribution of nuts on tree: Fairly well.

Tenacity: Good.

Hull:

*Texture.*—Smooth, strong and juicy when young. Wrinkled, soft and tattered towards ripening.

*Pits.*—Rare.

*Form.*—The shape of the nut.

*Thickness.*—Around 1 mm (0.04 inches).

*Suture.*—Hardly a distinct suture.

*Color.*—In May, half green (2.5 GY 9/8) and half red (2.5 R 4/10) with many white dots. In August, orange. At ripenting, fading orange.

*Dehiscence.*—At ripening, cracks in irregular lines.

*Tendency to Crack.*—No actual splitting by itself, but does crack or split according to the splitting endocarp.

Nut:

*Generally.*—Dry in shell. Quality of the nuts is excellent. Equals or above that of the 'Kerman' pistachio tree in almost all respects.

*Average weight.*—Dry in shell is 1.54 gr. 'Kerman' pistachio tree is 1.51 gr.

*Size—length.*—22 mm (0.88 inches).

*Size—width.*—14.3 mm (0.58 inches).

*Size—thickness.*—13.7 mm (0.56 inches).

*Form.*—Oblong, round.

*Color.*—Ivory.

*Pits.*—Rare.

*Base.*—Rough.

*Stem scar.*—Rough.

*Apex.*—Fully open (split).

*Inner surface.*—Smooth.

*Split.*—Over ninety percent (90%), by number, of the filled nuts are very well split. Almost ten percent (10%), by number, are closed.

*Percent by weight to kernel.*—53.3%.

*Percent by weight to shell.*—46.7%.

Kernel:

*Generally.*—From dry, in shell nuts.

*Size—Length.*—19.6 mm (0.08 inches).

*Size—Width.*—11.5 mm (0.47 inches).

*Size—Thickness.*—11 mm (0.45 inches).

*Form.*—Oblong.

*Thickness.*—11 mm (0.45 inches).

*Stem scar.*—Smooth.

*Apex.*—Roundish.

*Surface texture.*—Smooth.

*Kernel color.*—Green (5 GY 6/8).

*Numbers of doubles produced.*—Very rare.

*Flavor.*—Excellent. The natural flavor is much better than that of the 'Kerman' pistachio nuts.

*Eating quality.*—Excellent.

*Pellicle—color.*—Dark red.

*Pellicle—thickness.*—0.1 mm (0.004 inches).

*Pubescence.*—None.

Use: All uses and forms. From fresh to bakery and industrial food products, but mainly as a snack where salted and roasted.

Keeping quality: Very good.

Resistance to disease: Similar to the 'Kerman' pistachio tree and all other varieties.

Harvesting: Hand harvesting on small family plots. Mechanical harvesting in large scale farming operations.

Shipping and handling qualities: Very good.

Although the new variety of pistachio tree possesses the described characteristics noted above as a result of the growing conditions prevailing in Omer, Israel, it is to be understood that variations of the usual magnitude and characteristics incident to changes in growing conditions, irrigation, fertilization, pruning, pest control, climatic variation and the like are to be expected.

Having thus described and illustrated my new variety of pistachio tree, what I claim as new and desire to be secured by Plant Letters Patent is:

1. A new and distinct variety of pistachio tree substantially as illustrated and described which is somewhat remotely similar to the 'Kerman' pistachio tree, but from which it is distinguished in a number of respects including that the trees are capable of producing a high quality crop with many fewer hours of winter chilling; the trees are compact and thus can be planted in patterns of greater density; and by producing its crop which is mature for commercial harvesting and shipment approximately September 5, or about eight days earlier than the 'Kerman' pistachio tree in Omer, Israel.

* * * * *

UNITED STATES PATENT AND TRADEMARK OFFICE

CERTIFICATE OF CORRECTION

PATENT NO. : PP 10,275

DATED : March 10, 1998

INVENTOR(S) : Amram Nevo

It is certified that error appears in the above-identified patent and that said Letters Patent is hereby corrected as shown below:

Column 4, line 66, delete "beating" and substitute ---bearing---.

Column 5, line 11, delete "ripenting" and substitute ---ripening---.

Signed and Sealed this

Second Day of June, 1998

*Attest:*

*Attesting Officer*

BRUCE LEHMAN

*Commissioner of Patents and Trademarks*